United States Patent
Fuerst

(10) Patent No.: US 9,968,288 B2
(45) Date of Patent: May 15, 2018

(54) SYSTEMS AND METHODS FOR PREDICTING SEIZURES

(71) Applicant: Eco-Fusion, Ramat Gan (IL)

(72) Inventor: Oren Fuerst, Ramat Hasharon (IL)

(73) Assignee: Eco-Fusion, Ramat Gan (IL)

( * ) Notice: Subject to any disclaimer, the term of this patent is extended or adjusted under 35 U.S.C. 154(b) by 0 days. days.

(21) Appl. No.: 14/670,169

(22) Filed: Mar. 26, 2015

(65) Prior Publication Data

US 2015/0272494 A1    Oct. 1, 2015

Related U.S. Application Data

(60) Provisional application No. 61/970,470, filed on Mar. 26, 2014.

(51) Int. Cl.
*A61B 5/00*    (2006.01)
*A61B 5/0205*    (2006.01)
(Continued)

(52) U.S. Cl.
CPC ........ *A61B 5/4094* (2013.01); *A61B 5/02055* (2013.01); *A61B 5/746* (2013.01); *A61M 5/1723* (2013.01); *A61N 1/36064* (2013.01); *A61N 1/37258* (2013.01); *A61N 1/37282* (2013.01); *A61B 5/02405* (2013.01);
(Continued)

(58) Field of Classification Search
CPC ..... A61B 5/0205; A61B 5/7282; A61B 5/746; A61B 5/0022; A61B 5/1118; A61B 5/7246; A61B 5/7275; A61B 5/486; A61B 5/024; A61B 5/02055; A61B 5/01; A61B 5/02405; A61B 5/4836; A61B 5/0002; A61B 5/7264; A61B 5/0533; A61B 5/72; A61B 2505/07; A61B 5/0008; A61B 5/0015; A61B 5/04015; A61B 5/1114; A61B 5/1123; A61B 5/7271; A61B 5/747; A61B 5/00; A61B 5/0082; A61B 5/04; G06F 19/3406; A61N 1/37258; G06Q 50/24

See application file for complete search history.

(56) References Cited

U.S. PATENT DOCUMENTS 8,121,673 B2 *   2/2012   Tran ................. A61B 5/021
                                                     600/509
8,140,143 B2 *   3/2012   Picard ............... A61B 5/0531
                                                     600/382

* cited by examiner

*Primary Examiner* — Deborah Malamud
(74) *Attorney, Agent, or Firm* — Greenberg Traurig, LLP

(57) ABSTRACT

The present invention provides for a computer system including at least one server having software stored on a non-transient computer readable medium; where, upon execution of the software, the at least one server is at least configured to: i) receiving physiological data representative of a first physiological measurement of at least one physiological characteristic of an epileptic user; ii) receiving physiological data representative of a second physiological measurement of at least one physiological characteristic of the epileptic user; iii) comparing the first physiological measurement of the epileptic user to the second physiological measurement of the epileptic user; iv) based on the comparing, determining that a difference between the first physiological measurement of the epileptic user and the second physiological measurement is: a) higher than a predetermined threshold value, or b) smaller than the predetermined threshold value; and v) generating at least one alert; vi) transmitting the at least one alert.

12 Claims, 9 Drawing Sheets

(51) Int. Cl.
*A61M 5/172* (2006.01)
*A61N 1/36* (2006.01)
*A61N 1/372* (2006.01)
A61M 21/02 (2006.01)
A61B 5/024 (2006.01)
A61B 5/145 (2006.01)
A61B 5/11 (2006.01)
A61B 5/053 (2006.01)

(52) U.S. Cl.
CPC ......... *A61B 5/02416* (2013.01); *A61B 5/0533* (2013.01); *A61B 5/1101* (2013.01); *A61B 5/14542* (2013.01); *A61B 5/681* (2013.01); *A61B 5/7246* (2013.01); *A61B 5/7465* (2013.01); *A61M 21/02* (2013.01); *A61M 2205/054* (2013.01)

(1)

SYSTEMS AND METHODS FOR PREDICTING SEIZURES

RELATED APPLICATIONS

This application claims the priority of U.S. provisional application U.S. Patent Application No. 61/970,470; filed Mar. 26, 2014; entitled "SYSTEM AND METHOD OF PREDICTING EPILEPTIC SEIZURES AND ISSUING ASSOCIATED ALERTS," which is incorporated herein by reference in its entirety for all purposes.

TECHNICAL FIELD

In some embodiments, the instant invention is related to computer methods/systems to predict and alert about seizures.

BACKGROUND

Epilepsy is a group of neurological disorders characterized by epileptic seizures. Epileptic seizures are episodes that can vary from brief and nearly undetectable to long periods of vigorous shaking. In epilepsy, seizures tend to recur, and have no immediate underlying cause while seizures that occur due to a specific cause are not deemed to represent epilepsy.

SUMMARY OF INVENTION

In some embodiments, the instant invention provides for a computer system, including: a) at least one server having software stored on a non-transient computer readable medium; where, upon execution of the software, the at least one server is at least configured to: i) receiving, in real-time, physiological data representative of a first physiological measurement of at least one physiological characteristic of the user, wherein the at least one physiological characteristic is selected from the group consisting of: heart rate, heart rate variability, oxygen saturation, temperature, hand movement, body movement, galvanic skin response, or any combination thereof; ii) receiving, in real-time, physiological data representative of a second physiological measurement of at least one physiological characteristic of the user, wherein the at least one physiological characteristic is selected from the group consisting of: heart rate, heart rate variability, oxygen saturation, temperature, hand movement, galvanic skin response, or any combination thereof; iii) comparing, in real-time, the first physiological measurement of the user to the second physiological measurement of the user; iv) based on the comparing, determining, in real-time, that a difference between the first physiological measurement of the user and the second physiological measurement is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a method of treatment, including: when at least one alert generated by at least one wearable computing device is received by a user, administering an effective amount of an epileptic-directed treatment to the user so as to reduce a severity or occurrence of an imminent epileptic seizure, where the epileptic-directed treatment is selected from the group consisting of an epileptic-directed medication, electrotherapy, relaxation therapy, and breathing therapy, where the at least one alert is generated regarding at least one physiological condition; where the at least one alert is generated when a measurement of the at least one physiological condition is higher than at least one predetermined threshold measurement, where the at least one physiological condition of the user is selected from the group consisting of: heart rate, heart rate variability, oxygen saturation, PPG signal, temperature, hand movement, galvanic skin response, or any combination thereof, where at least one alert is transmitted to at least one of: the user, at least one family member, at least one medical practitioner, or any combination thereof, and where, when the measurement of the at least one physiological condition is smaller than the predetermined threshold measurement, continuing to measure the at least one physiological condition of the user. In some embodiments, the at least one alert is further generated when a first physiological measurement is compared to a second physiological measurement, the second physiological measurement is selected from the group consisting of: heart rate, heart rate variability, oxygen saturation, temperature, hand movement, galvanic skin response, PPG signal, or any combination thereof, the at least one alert is generated when a difference between the first physiological measurement of the user and the second physiological measurement is higher than a predetermined threshold value.

In some embodiments, the instant invention provides for a computer method, including: i) receiving, in real-time, physiological data representative of a first physiological measurement of at least one physiological characteristic of the user, wherein the at least one physiological characteristic is selected from the group consisting of: heart rate, heart rate variability, oxygen saturation, temperature, hand movement, body movement, galvanic skin response, or any combination thereof; ii) receiving, in real-time, physiological data representative of a second physiological measurement of at least one physiological characteristic of the user, wherein the at least one physiological characteristic is selected from the group consisting of: heart rate, heart rate variability, oxygen saturation, temperature, hand movement, galvanic skin response, or any combination thereof; iii) comparing, in real-time, the first physiological measurement of the user to the second physiological measurement of the user; iv) based on the comparing, determining, in real-time, that a difference between the first physiological measurement of the user and the second physiological measurement is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer system, including: a) at least one server having software stored on a non-transient computer readable medium; where, upon execution of the software, the at least one server is at least configured to: i) receiving, an input from a user, where the input includes user data consisting of: food intake of the user, medication intake by the user, stress related events in the preceding day, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, an input from a user or from his medical record, where the input includes user data consisting of: food intake of the user, stress related events in the preceding day, medication intake by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer system, including: a) at least one server having software stored on a non-transient computer readable medium; where, upon execution of the software, the at least one server is at least configured to: i) receiving, in real-time, an input from a user, where the input includes user data consisting of: food intake of the user, medication intake by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, in real-time, an input from a user, where the input includes user data consisting of: food intake of the user, medication intake by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

An embodiment of the present invention is a computer-implemented method, comprising: receiving, by a specifically programed processing computer system, from an electronic monitoring system, at least two of the following: i) a first data from the electronic monitoring system, wherein the first data from the electronic monitoring system is selected from the group consisting of: a first heart beat, a first heart beat variability, a first low frequency heart beat variability, a first high frequency heart beat variability, a first level of movement, and a first blood saturation level, and ii) a second data from the electronic monitoring system, wherein the second data from the electronic monitoring system is selected from the group consisting of: a second heart beat, a second heart beat variability, a second low frequency heart beat variability, a second high frequency heart beat variability, a second level of movement, and second blood saturation level; comparing the first data from the electronic monitoring system to the second data from the electronic monitoring system, wherein the electronic monitoring system identifies at least one deviation of a user, wherein the user is patient diagnosed with epilepsy; sending, by the specifically programed processing computer system, at least one alert to at least one designated responder, wherein the at least one designated responder is selected from the group consisting of: a member of a medical team and a member of the family; generating, in response to the receiving the alert by the specifically programed processing computer system, a notification to the at least one designated responder; sending, by the specifically programed processing computer system, the notification to the at least one designated responder; receiving, by the at least one designated responder, the notification; wherein the at least one designated responder receives the notification by the specifically programed processing computer system.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DESCRIPTION OF EXEMPLARY EMBODIMENTS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the present invention is an alert mechanism for epilepsy. In some embodiments, the present invention is a non-invasive alert system for epilepsy. In some embodiments, the present invention is an alarm system. In some embodiments, the present invention is configured to save the lives of people suffering from epilepsy.

In some embodiments, the present invention is an alert mechanism for epilepsy. In some embodiments, the alert mechanism is based on a deviation from the calculated expected value of at least one of the following: heart beat, heart beat variability, low frequency heart beat, high frequency heart beat variability, level of movement, and blood saturation level. In some embodiments, the present invention is based on at least one of the following input parameters: food eaten prior to going to sleep, physical activity during the preceding day, and stress level prior to going to sleep.

Figure 1:
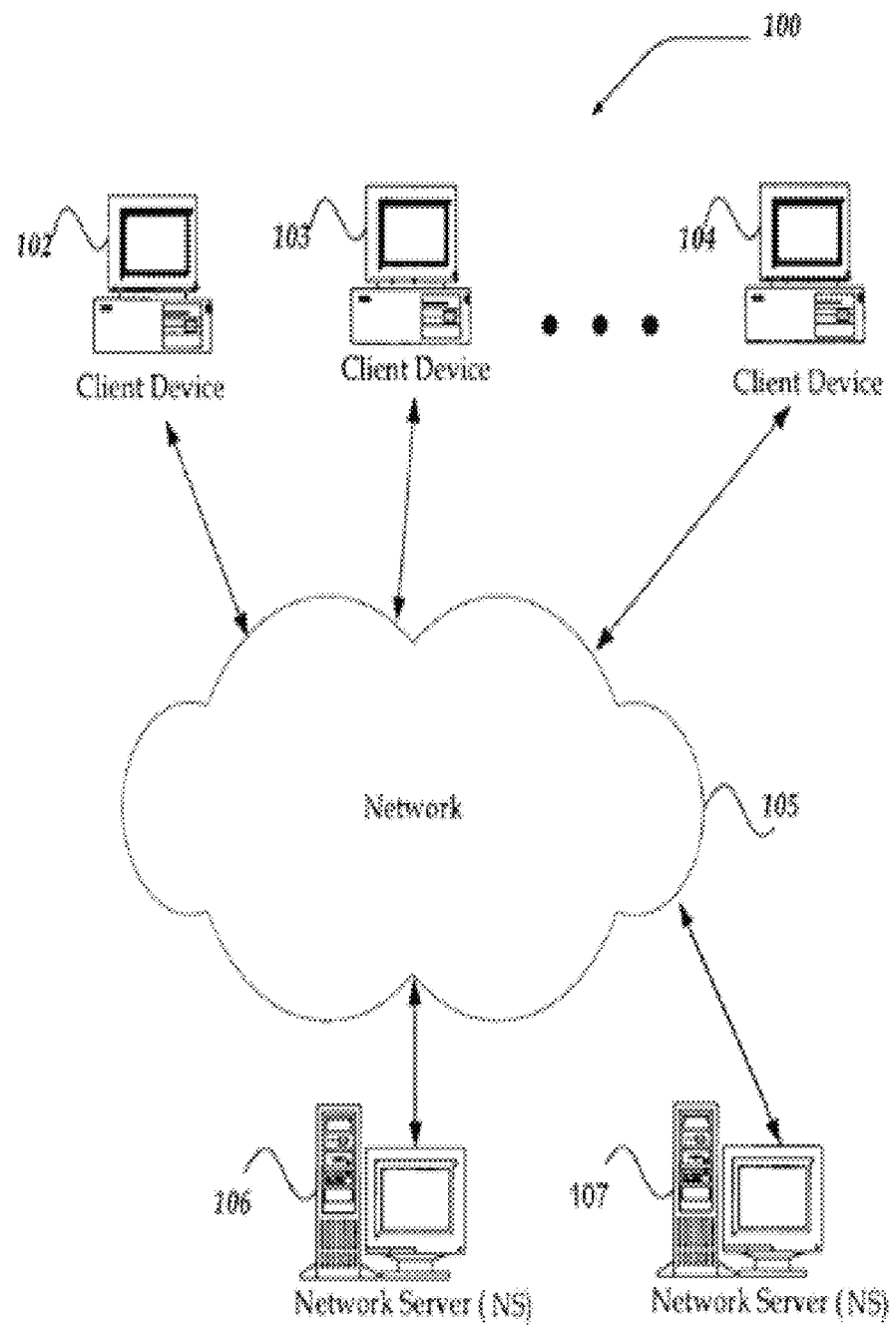
FIGS. 1 and 2 illustrates some embodiments of the inventive system of the present invention, showing users suffering from epilepsy connecting over network servers in accordance with the invention.

FIG. 1 illustrates an embodiment of the present invention.

Figure 2:
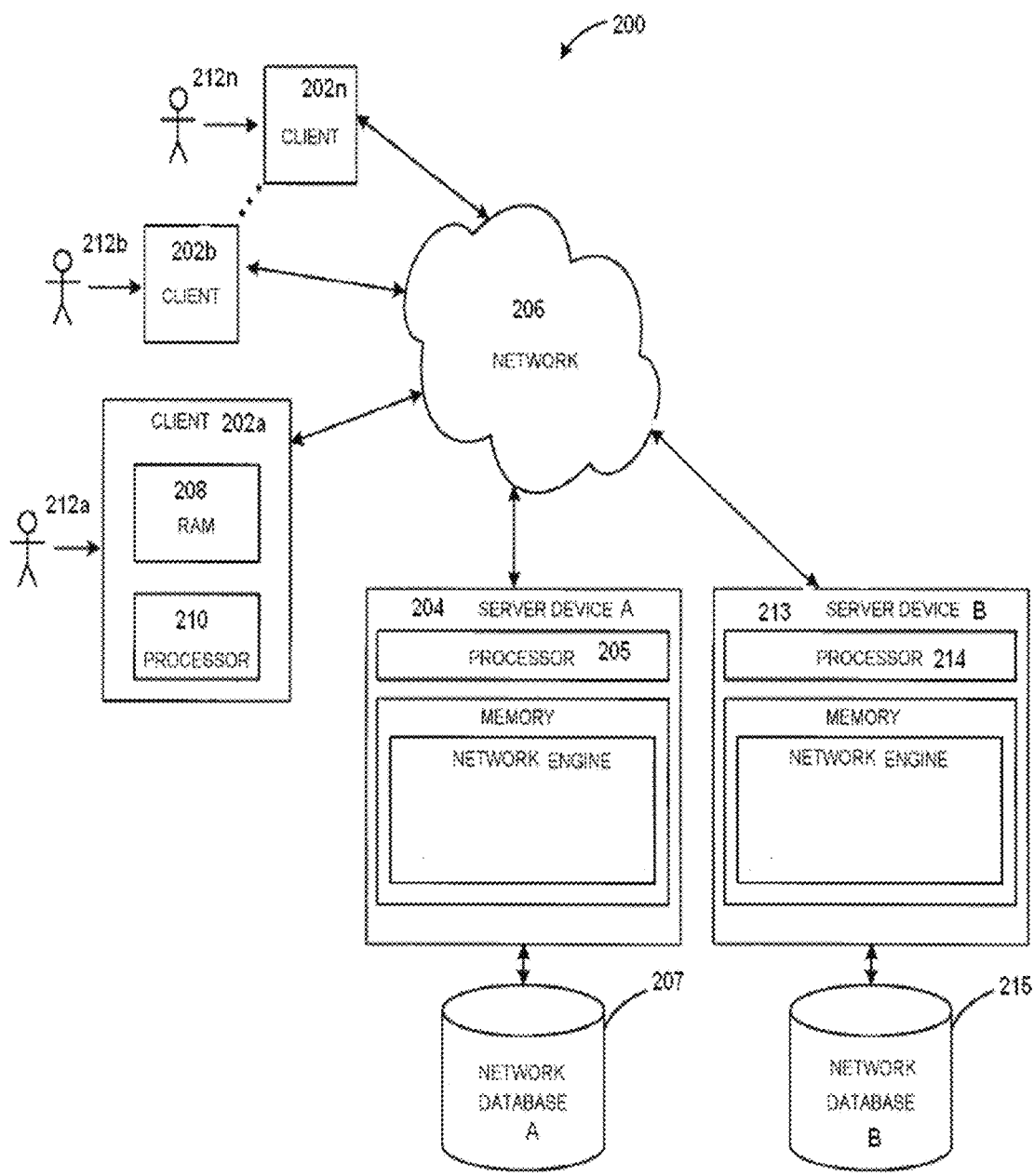

FIG. 2 illustrates an embodiment of the network architecture of the present invention.

Figure 3:
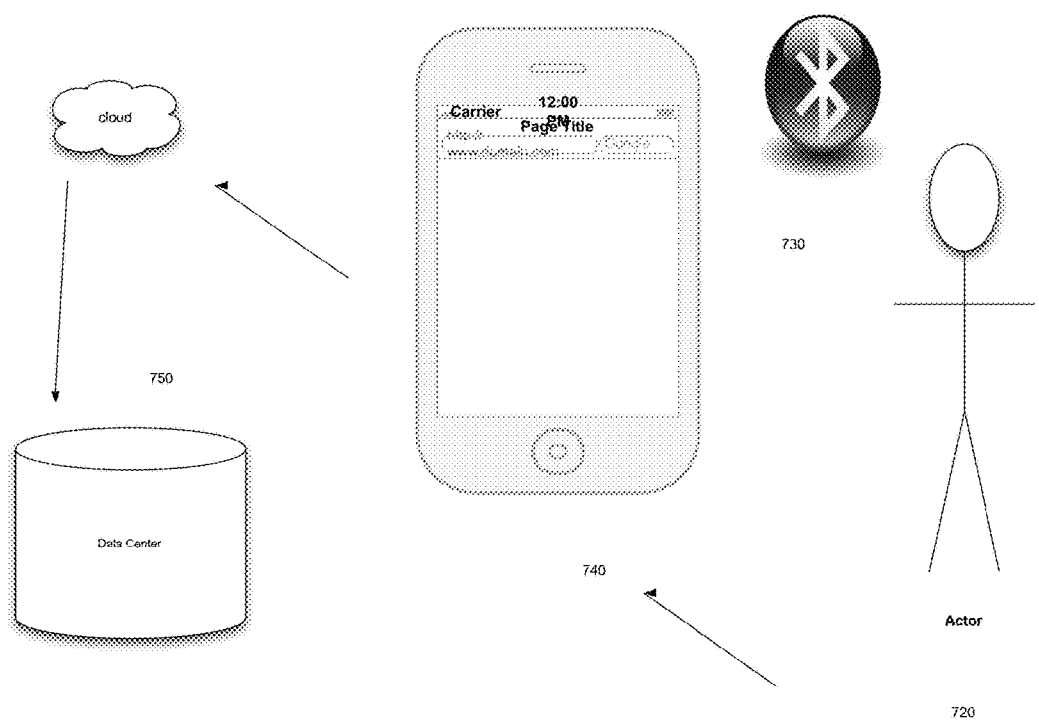
FIG. 3 illustrates some embodiments of the inventive system of the present invention, showing a system receiving inputs provided by a user diagnosed with epilepsy.

FIG. 3 illustrates an embodiment of the system of the present invention.

Figure 4:
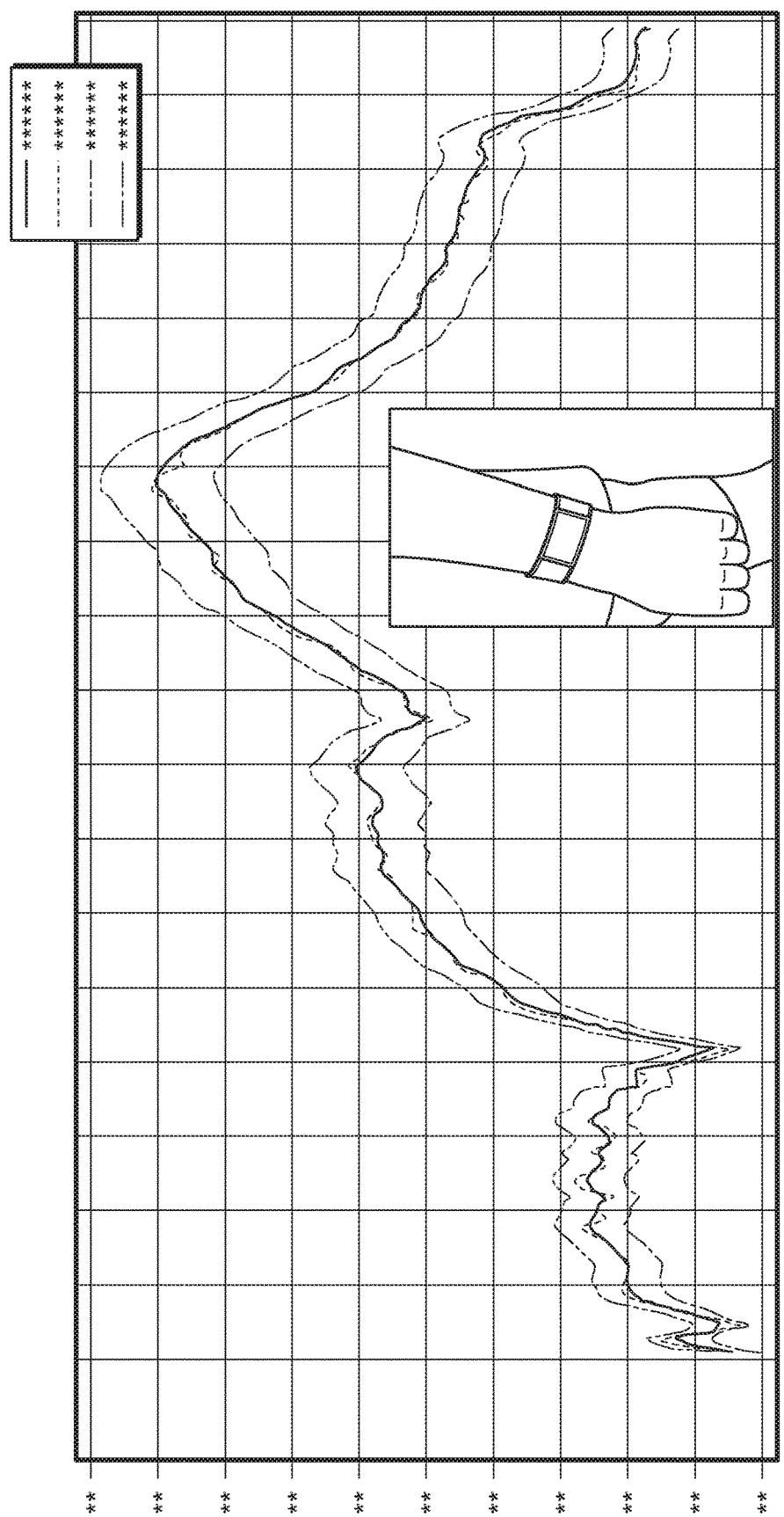
FIG. 4 illustrates some embodiments of the inventive system of the present invention, showing a wristband configured to include the system of the present invention.

FIG. 4 is an embodiment of a hand with the wristband.

Figure 5:
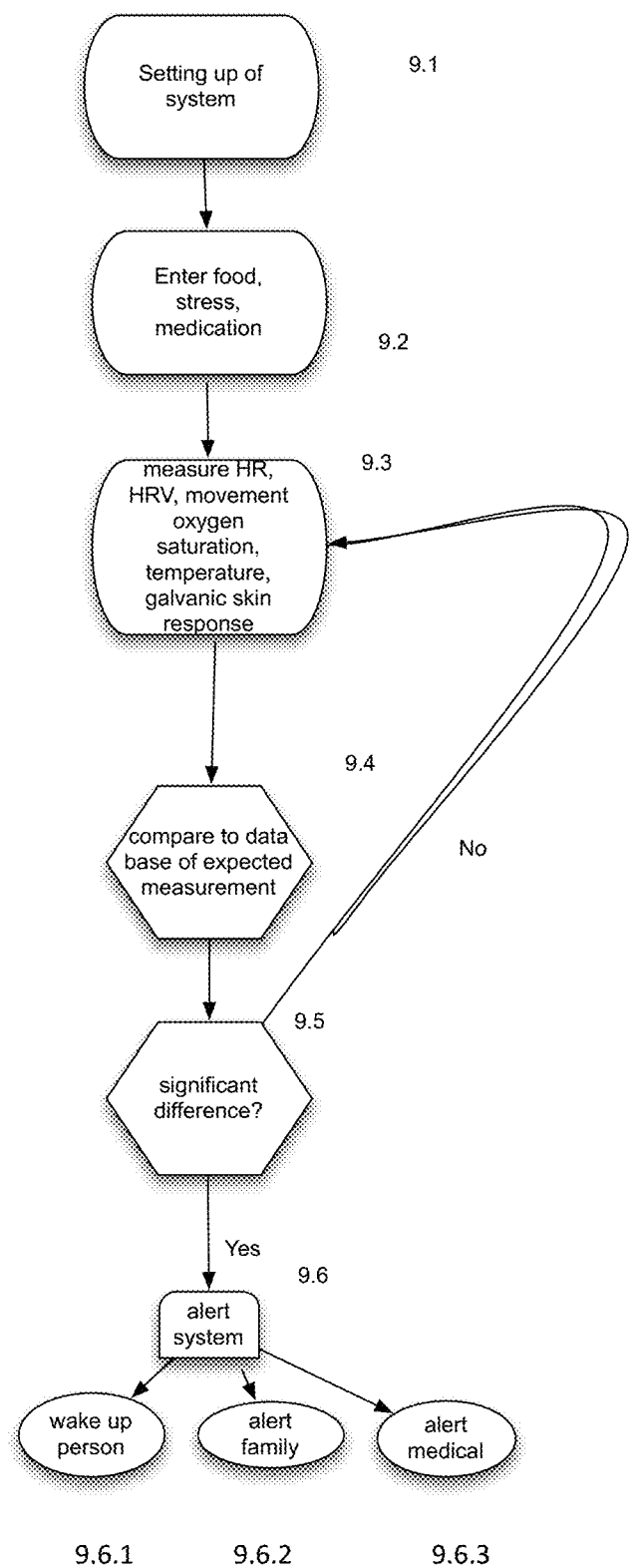
FIG. 5 illustrates a flow diagram of an embodiment of the inventive system of the present invention.

FIG. 5 is a block flow diagram of the process of the present invention.

Figure 6:
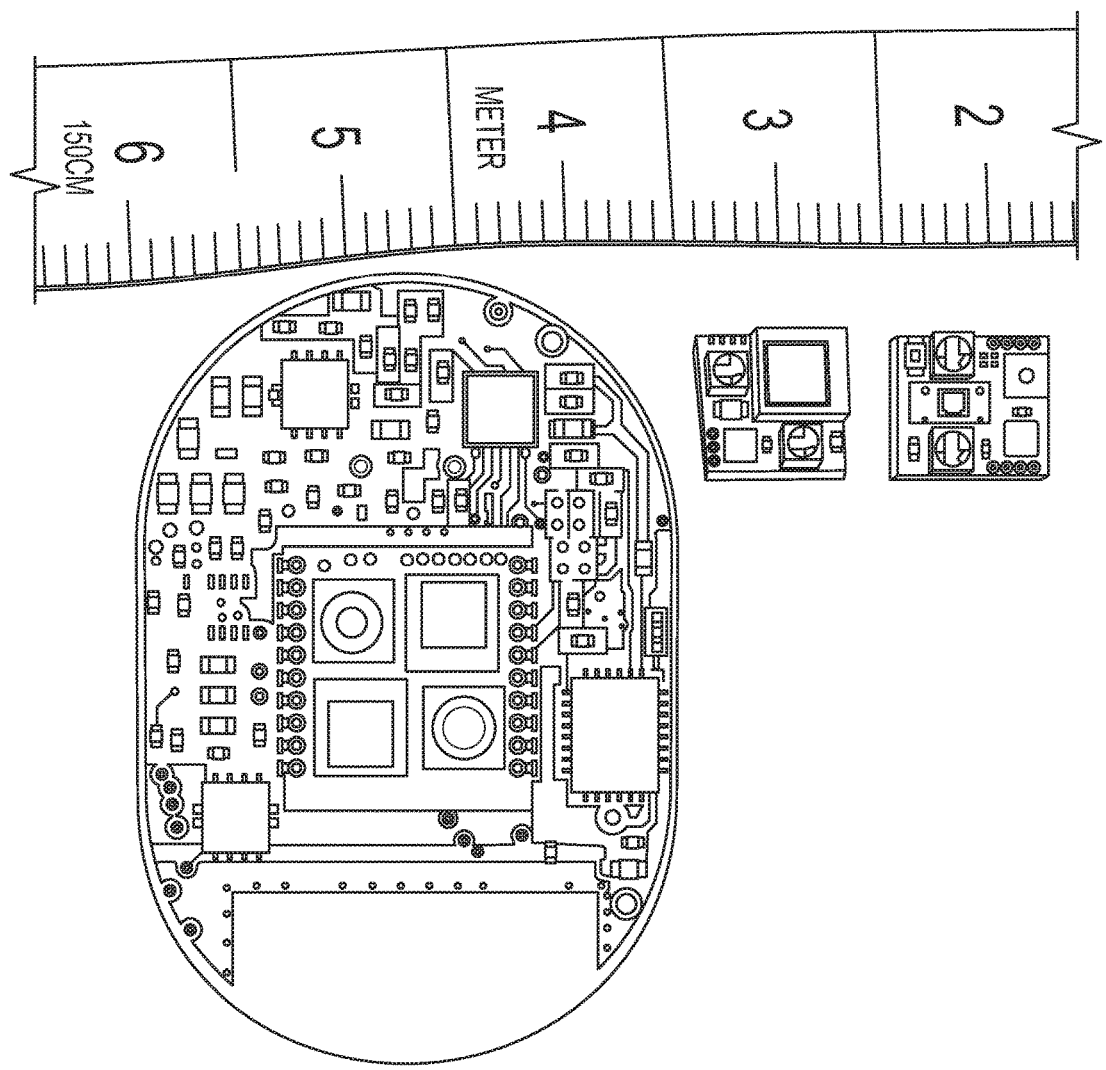
FIG. 6 illustrates an embodiment of the inventive system of the present invention, showing sensors for use in connection with the system.

FIG. 6 is an embodiment of a view of a sample of typical PPG (Photoplethysmography) sensors with Motion immunity using a 3d Accelerometer sensor. In some embodiments, the sensor can be used as a sensor to detect Heart Rate Variability (HRV) and movement of the hand. In some embodiments, additional sensors can be added to include other parameters, such as blood oxygen.

Figure 7:
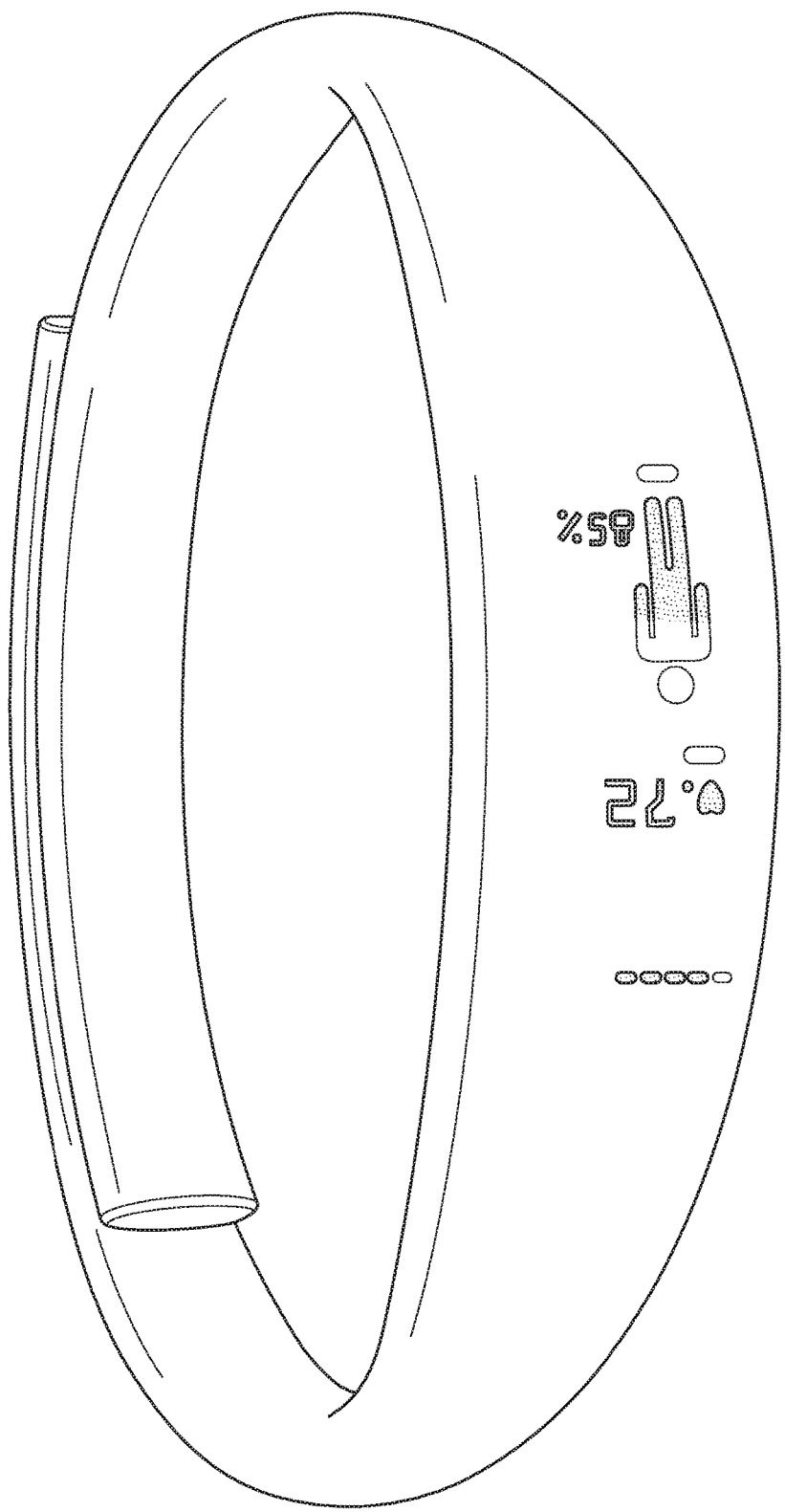
FIG. 7 illustrates an embodiment of a watch configured to use the inventive system.

FIG. 7 illustrates an embodiment of a wrist-band of the present invention.

Figure 8:
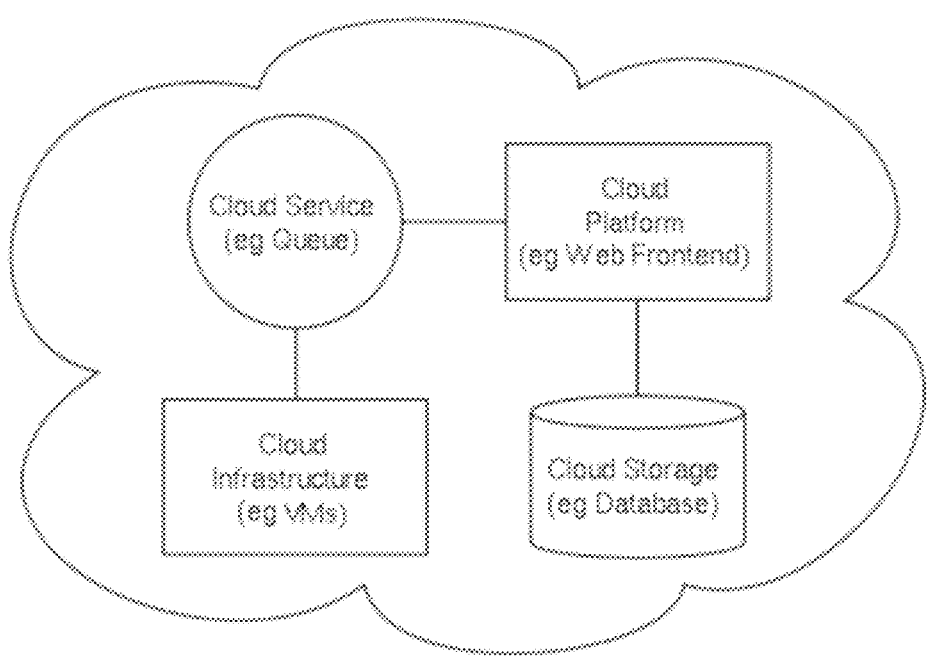
FIGS. 8 and 9 illustrate some embodiments of the system of the present invention.
Figure 9:
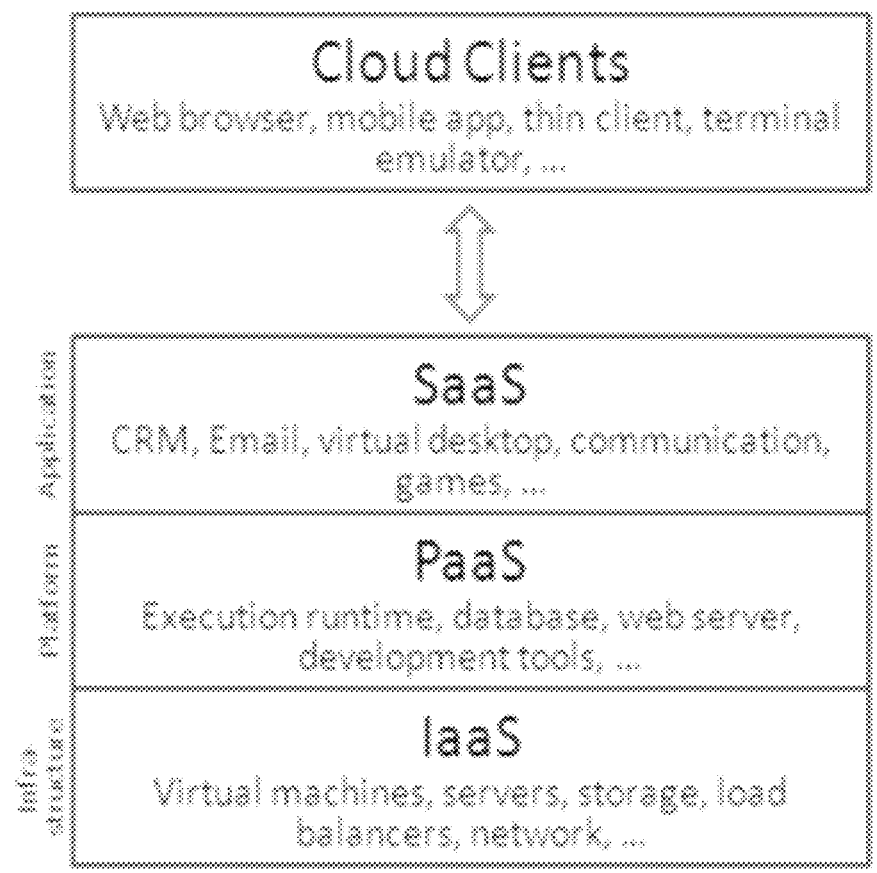

FIGS. 8 and 9 illustrate some further aspects of some embodiments of the present invention.

Epileptic Seizures

In some embodiments, the inventive system of the present invention allows for the monitoring of symptoms of epileptic seizures, which may be idiosyncratic/unique/personalized to a person, but people generally learn to recognize his/her unique symptoms. In some embodiments, symptoms of epileptic seizures are neurogenic (autonomic) symptoms which, for example, may include, but are not limited to, palpitations, tremor, hunger, and sweating. In some embodiments, neuroglycopenic symptoms typically include behavioral changes, difficulty thinking, confusion, or any combination thereof. In some embodiments, neuroglycopenic manifestations can include seizure, coma, and even death.

In some embodiments, the system of the present invention is configured to identify heart rate (HR) variability, which is typically used to detect autonomic dysfunction in clinical settings. In some embodiments, patients suffering from epilepsy may exhibit a marked decrease in the low-frequency component of heart rate variability during spontaneous epileptic seizure. In some embodiments, the correlation of a decrease in the low-frequency component of heart rate variability with an epileptic seizure events can serve as a prediction mechanism, where additional medical and non medical parameters can be utilized as additional parameters in order to define a pathway for the HRV during the day or night, and hence to look for deviations from the pathway that will trigger a plurality of alerts, as such deviations may indicate an epileptic seizure.

In some embodiments, the present invention is an alert system configured to obtain/receive and/or store/record: (i) the food intake of the user, (ii) the medication taken by the user, and (iii) heart rate and/or heart rate variability parameters of the user. In an embodiment, the system is configured to calculate an expected heart rate and/or heart rate variability, and where an identification of extreme deviations from these values occurs, the system is configured to create and/or deliver an epileptic seizure alert to a user, an emergency contact(s), a doctor, a hospital, or any combination thereof. In some embodiments, the calculation of heart rate and/or heart rate variability occurs after a measurement of a person's heart rate is recorded by the system. In some embodiments, the system is configured to obtain, record, calculate, or any combination thereof, a plurality of measurements from a plurality of samples obtained during a plurality of time points.

FIG. 3 illustrates an embodiment of the system of the present invention. FIG. 3 shows, as a non-limiting example, a wristband (the system of the present invention can also be combined in an armband or any other non-invasive wearable sensor) 710 worn by a user 720, where the wristband is configured to communicate by a communication standard such as, but not limited to, Bluetooth 730 with a mobile device such as, but not limited to, an iPhone 740. In an embodiment, the system includes a mobile device 740 which is configured to incorporate an application/software configured to capture a plurality of bio-signals, e.g., but not limited to, heart rate and the heart rate variability of a user, generated/obtained from the wristband 710. In an embodiment, the system is configured to obtain additional biosignals captured from a user's body from a plurality of sensors housed on the wristband including, but not limited to, blood oxygen, galvanic response, skin temperature, or any combination thereof.

FIG. 4 illustrates an embodiment of the system of the present invention, where the system is configured to calculate heart rate variability by use of, e.g., but not limited to, the mobile device, where the heart rate variability is measured and identified by the system when the frequency of the heart beat-to-beat sampling is sufficiently/substantially high, for example, but not limited to, a measurement of about 108 hz. In another embodiment, the system is configured to send information/data from an application/software to, e.g., but not limited to, a Data Center 750, where the Data Center manages Big Data analysis. In an embodiment, information/data is managed by: (i) being stored and/or compared to a plurality of users' data, (ii) benchmarking the user's data to the user's historical data, (iii) back-testing, (iv) storing, (v) routing data/information to medical personnel (e.g., but not limited to, doctors, nurses, nurse practitioners, EMTs, etc., or any combination thereof), or any combination thereof.

In some embodiments, the system of the present invention is configured to identify/measure a sudden drop in the heart rate variability and/or component(s) of heart rate variability (e.g., but not limited to, the low frequency component(s)), where the sudden drop in the heart rate variability and/or component of heart rate variability is/are an indication(s) of a forthcoming epileptic seizure event. In some embodiments, the system includes an alert configured to trigger an alarm on, e.g., but not limited to, at least one mobile phone. In some embodiments, the system is configured to send at least one alert/a plurality of alerts to at least one medical team and/or at least one family member of the user.

FIG. 5 illustrates an embodiment of the system of the present invention, including an initial setting up phase 9.1, where the system is configured to receive a plurality of inputs provided/delivered by a user which define his preference set, for example, but not limited to, medications, including dosing and morning/afternoon/evening medication, favorite foods, glycemic index for different foods if needed, for example, when the user's known digestion is different from the otherwise known glycemic index. In another embodiment, at step 9.2, the system is configured to receive a user's entry/input, where the user's entry/input can be the user's last food intake before going to sleep, stress level (if, for example, the wrist band was not worn during the day and the information was not captured during the day by the system already), information regarding medications taken and which might still be influencing the likelihood of an epileptic seizure (such as, e.g., but not limited to, stress and anxiety reducing medication). In an embodiment, at stage 9.3, the system is configured to continuously analyze information/data input and/or collected from the wrist band. In another embodiment, the information/data can include multi-parameters from at least one of the following measurements: beat-to-beat heart rate, heart rate variability and heart rate variability components, oxygen level, skin temperature, galvanic skin response, or any combination thereof. In another embodiment, the system is configured to analyze the information/data for changes/deviations compared with an expected information/data projected for the same time during the night sleep or during the day for the same user when compared to a benchmark on the data base, which is located at the mobile device 740 and the data center 750 and/or the cpu level located on the wrist band 710. In some embodiments, the expected value can be derived many different ways, for example using the historical pattern of the same user or similar users or patients given similar scenarios of food intake and heart rate and stress level readings before going to sleep. In some embodiments, a pathway of a reading of 120 with a stressful day (as measured by, e.g., but not limited to, questionnaires and HRV or galvanic skin readings) and an evening meal filled with carbs will be compared to a population of similar pattern. In some embodiments, pattern recognition and parameters of interest may correlate to the above parameters but can correlate to combination of parameters, as such parameters may arise from statistical analysis using tools such as discriminant, neural network or principal component analysis.

In an embodiment, the system is configured to compare the calculated expected values with the actual. In an embodiment, the system is configured to receive/record/account the prior information known about the user, such as, but not limited to, the food eaten in the meal prior to going to sleep. In an embodiment, the system is configured to trigger and/or send at least one alert (e.g., 1, 2, 3, 4, 5, 6, 7, 8, 9, 10 etc. alerts) when, according to the comparison of the system noted in 9.5, there is a substantially significant change from what would have been expected, to: wake up the person 9.6.1, to alert the family, 9.6.2, alert the medical team 9.6.3, or any combination thereof.

In another embodiment, the system of the present invention includes triggers for an alarm which is configured to be adjusted based on the habits of the user.

In some embodiments, the amount of food and medication prior to going to sleep will have an impact on the probability of an epileptic attack and the time during sleep, if at all, of an epileptic attack event to occur. In some embodiments, additional events on the day prior to the night sleep influence the likelihood of epileptic seizure to occur. In some embodiment, levels of stress are configured to be measured by the wristband by the HRV that was measured during the preceding day, as captured by the application/software of the system. In an embodiment, there is a correlation between higher the level of stress and the higher occurrence for a epileptic seizure event.

The Autonomic Nervous System (ANS)

Table 1 outlines which organs are affected by the sympathetic (SNS) and parasympathetic (PSNS) nervous systems. Typically, the SNS initiates a "fight or flight" response to stress. The SNS increases heart rate, dilates or opens the lungs, inhibits digestion and dilates the pupils, providing the body with the resources it needs to protect itself in times of danger. The PSNS conversely, is known as the "rest and digest" system; it promotes digestion, reduces heart rate, increases salivation, increases urine secretion from the kidneys and constricts the pupils. On a day-to-day basis, these two pathways work in parallel to maintain homeostatic balance within the body.

TABLE 1

| Hormone | Blood | Mechanism of Action | |
|---|---|---|---|
| | | Inhibition of gluconeogenesis (liver) | Glucose entry stimulation (muscle) |
| Insulin | ↓ | Stimulation of glucose storage, glycogen formation (liver, muscle) | — |
| Adrenaline | ↑ | — | Stimulation of glycogen breakdown to active molecules (liver, muscle) |
| Glucagon | ↑ | Stimulation of glucose storage (liver) Stimulation of glucose formation from non-carbohydrate substrates (liver) | — |
| Cortisol | ↑ | — | Stimulation of glucose formation from non-carbohydrate substrates (liver) |
| Growth hormone | ↑ | — | Mobilization of triglycerides |

Heart Rate Variability (HRV) and Epilepsy

In some embodiments, the system of the present invention is configured to identify a correlation between probability and timing of epileptic seizure, HRV and other physiological parameters. For example, patients suffering from Epilepsy show lower than average HRV.

Epileptic seizures are typically joined by changes in bodily functions such as, but not limited to, changes in heart rate (HR), Heart Rate Variability (HRV) and also drive changes in ANS. Such changes can occur prior, during, after, or any combination thereof, the seizure.

For example, disorders of the cardiovascular system and other autonomic nervous system functions are often found in patients with temporal lobe epilepsy (TLE). Traditional time and frequency domain measures of heart rate (HR) variability (extracted from ECG recordings) were lower in patients with TLE than in controls ($p<0.05$). In addition, the power law slope ($p<0.005$) and ApEn ($p<0.05$) were also reduced in TLE patients. The table below details heart rate and measures of heart rate variability in patients with TLE and control subjects:

| Measure/ variable | Patients with refractory TLE (n = 9) | Patients with well controlled TLE (n = 25) | All patients (n = 44) | Control subjects (n = 4) | p Value‡ (Mann-Whitney) |
|---|---|---|---|---|---|
| RRI (ms) | 863 (103) | 819 (112) | 838 (109) | 850 (71) | 0.403 |
| SDNN (ms) | 154 (32) | 158 (51) | 156 (43) | 177 (44) | 0.039 |
| VLF (ms$^2$) | 1538 (762) | 1749 (1005) | 1658 (905) | 3256 (1765) | <0.001 |
| LF (ms$^2$) | 905 (472) | 1038 (507) | 981 (491) | 1901 (1308) | 0.001 |
| HF (ms$^2$) | 604 (502) | 628 (365) | 618 (424) | 1710 (2050) | 0.011 |
| ApEn | 0.93 (0.21)† | 1.09 (0.32) | 1.02 (0.29) | 1.15 (0.21) | 0.045 |
| α1 | 1.22 (0.18) | 1.17 (0.18) | 1.19 (0.18) | 1.16 (0.1) | 0.292 |
| α2 | 1.03 (9.0) | 0.99 (7.64)* | 1.01 (8.45) | 1.01 (6.13) | 0.824 |
| Slope of HRV | −1.32 (0.13) | −1.37 (0.21) | −1.35 (0.18) | −1.20 (0.21) | 0.002 |

Values are mean (SD); RRI, R-R Interval; SDNN, SD of all RRIs; VLF, very low frequency; LF, low frequency; HF, high frequency; ApEn, approximate entropy; α1, short term scaling exponent; α2, long-term scaling exponent;
*p = 0.037 compared with the patients with refractory TLE;
†p = 0.021 compared to the patients with well controlled TLE;
‡ all patients compared with the control subjects.

Power spectral analysis of HR variability (power in ms^2) is shown on the table above. The area under the spectral curve from 0.005 to 0.04 Hz represents VLF power, the area from 0.04 to 0.15 represents LF power, and the area from 0.15 to 0.4 Hz represents HF power. Patients suffering from TLE show a typical suppression of all the power spectral components of HR variability. RRI indicates RR interval.

Examples of alerts indicating an imminent epileptic attack(s)/seizure(s) could be set based on the data for patients with refractory TLE, patients with well controlled TLE. As an exemplary embodiment, an alert indicating an imminent epileptic attack/seizure could be triggered when HF is at least 20% below the mean expected HF (ms^2) for patients with refractory TLE, in this case 480 ms^2 (versus expected 600). In another exemplary embodiment, would be LF of at least 25% below the expected norm of 900, meaning 675 ms^2.

In some embodiments, an alert indicating an imminent epileptic attack/seizure could be triggered when HF is between 20%-99% below the mean expected HF (ms^2) for patients with refractory TLE. In some embodiments, an alert could be triggered when HF is between 30%-99% below the mean expected HF (ms^2) for patients with refractory TLE. In some embodiments, an alert could be triggered when HF is between 40%-99% below the mean expected HF (ms^2) for patients with refractory TLE. In some embodiments, an alert could be triggered when HF is between 50%-99% below the mean expected HF (ms^2) for patients with refractory TLE. In some embodiments, an alert could be triggered when HF is between 60%-99% below the mean expected HF (ms^2) for patients with refractory TLE. In some embodiments, an alert could be triggered when HF is between 70%-99% below the mean expected HF (ms^2) for patients with refractory TLE. In some embodiments, an alert could be triggered when HF is between 80%-99% below the mean expected HF (ms^2) for patients with refractory TLE. In some embodiments, an alert could be triggered when HF is between 90%-99% below the mean expected HF (ms^2) for patients with refractory TLE. In some embodiments, an alert could be triggered when HF is between 20%-90% below the mean expected HF (ms^2) for patients with refractory TLE. In some embodiments, an alert could be triggered when HF is between 20%-80% below the mean expected HF (ms^2) for patients with refractory TLE. In some embodiments, an alert could be triggered when HF is between 20%-70% below the mean expected HF (ms^2) for patients with refractory TLE. In some embodiments, an alert could be triggered when HF is between 20%-60% below the mean expected HF (ms^2) for patients with refractory TLE. In some embodiments, an alert indicating an imminent epileptic attack/seizure could be triggered when HF is between 20%-50% below the mean expected HF (ms^2) for patients with refractory TLE. In some embodiments, an alert could be triggered when HF is between 20%-40% below the mean expected HF (ms^2) for patients with refractory TLE. In some embodiments, an alert could be triggered when HF is between 20%-30% below the mean expected HF (ms^2) for patients with refractory TLE. In some embodiments, an alert could be triggered when HF is between 30%-90% below the mean expected HF (ms^2) for patients with refractory TLE. In some embodiments, an alert could be triggered when HF is between 40%-80% below the mean expected HF (ms^2) for patients with refractory TLE. In some embodiments, an alert could be triggered when HF is between 50%-70% below the mean expected HF (ms^2) for patients with refractory TLE.

In some embodiments, an alert indicating an imminent epileptic attack/seizure could be triggered when LF is between 25%-99% below expected LF (ms^2) for patients with refractory TLE. In some embodiments, an alert could be triggered when LF is between 30%-99% below expected LF (ms^2) for patients with refractory TLE. In some embodiments, an alert could be triggered when LF is between 40%-99% below expected LF (ms^2) for patients with refractory TLE. In some embodiments, an alert could be triggered when LF is between 50%-99% below expected LF (ms^2) for patients with refractory TLE. In some embodiments, an alert could be triggered when LF is between 60%-99% below expected LF (ms^2) for patients with refractory TLE. In some embodiments, an alert could be triggered when LF is between 70%-99% below expected LF (ms^2) for patients with refractory TLE. In some embodiments, an alert could be triggered when LF is between 80%-99% below expected LF (ms^2) for patients with refractory TLE. In some embodiments, an alert could be triggered when LF is between 90%-99% below expected LF (ms^2) for patients with refractory TLE. In some embodiments, an alert could be triggered when LF is between 25%-90% below expected LF (ms^2) for patients with refractory TLE. In some embodiments, an alert could be triggered when LF is between 25%-80% below expected LF (ms^2) for patients with refractory TLE. In some embodiments, an alert could be triggered when LF is between 25%-70% below expected LF (ms^2) for patients with refractory TLE. In some embodiments, an alert could be triggered when LF is between 25%-60% below expected LF (ms^2) for patients with refractory TLE. In some embodiments, an alert could be triggered when LF is between 25%-50% below expected LF (ms^2) for patients with refractory TLE. In some embodiments, an alert could be triggered when LF is between 25%-40% below expected LF (ms^2) for patients with refractory TLE. In some embodiments, an alert could be triggered when LF is between 25%-30% below expected LF (ms^2) for patients with refractory TLE. In some embodiments, an alert could be triggered when LF is between 30%-90% below expected LF (ms^2) for patients with refractory TLE. In some embodiments, an alert could be triggered when LF is between 40%-80% below expected LF (ms^2) for patients with refractory TLE. In some embodiments, an alert could be triggered when LF is between 30%-90% below expected LF (ms^2) for patients with refractory TLE. In some embodiments, an alert could be triggered when LF is between 40%-80% below expected LF (ms^2) for patients with refractory TLE. In some embodiments, an alert could be triggered when LF is between 50%-70% below expected LF (ms^2) for patients with refractory TLE.

In some embodiments, the sympathetic nervous system is one of the two main divisions of the autonomic nervous system, the other being the parasympathetic nervous system. The autonomic nervous system functions to regulate the body's unconscious actions. The sympathetic nervous system's primary process is to stimulate the body's fight-or-flight response. It is, however, constantly active at a basic level to maintain homeostasis. The sympathetic nervous system is complementary to the parasympathetic nervous system which stimulates the body to "rest-and-digest" or "feed and breed". It increases during excitement and also with physical or mental. The only organ that is purely innervated by the sympathetic nervous system (and not affected by parasympathetic activation) is the skin. In some embodiments, an increase in sympathetic activation can be observed by monitoring subtle electrical changes across the surface of the skin. In an exemplary embodiment, during an epileptic seizure, an average amplitude of EDA was 8.15 microSiemens (0.60-20.95), where the siemens (SI unit symbol: S) is the unit of electric conductance, electric susceptance and electric admittance in the International System of Units (SI). In some embodiments, an alert would be triggered when an EDA measurement exceeds 6 microsiemens. In some embodiments, a combination of parameters such as hand or body movement, components of HRV, EDA (electrodermal activity), or any combination thereof, could be derived as combined factors in a linear or non-linear way (using tools such as, but not limited to, neural network and factor analysis).

In some embodiments, additional measurements such as, but not limited to, skin conductivity could be used as part of a trigger or alert mechanism. For example, EDA rises during epilepsy seizures. In some embodiments, an alert indicating an imminent epileptic attack/seizure could be triggered when an EDA measurement rises between 10-99% compared with an expected EDA measurement. In some embodiments, an alert could be triggered when an EDA measurement rises between 20-99% compared with an expected EDA measurement. In some embodiments, an alert could be triggered when an EDA measurement rises between 30-99% compared with an expected EDA measurement. In some embodiments, an alert could be triggered when an EDA measurement rises between 40-99% compared with an expected EDA measurement. In some embodiments, an alert could be triggered when an EDA measurement rises between 50-99% compared with an expected EDA measurement. In some embodiments, an alert could be triggered when an EDA measurement rises between 60-99% compared with an expected EDA measurement. In some embodiments, an alert could be triggered when an EDA measurement rises between 70-99% compared with an expected EDA measurement. In some embodiments, an alert could be triggered when an EDA measurement rises between 80-99% compared with an expected EDA measurement. In some embodiments, an alert could be triggered when an EDA measurement rises between 90-99% compared with an expected EDA measurement. In some embodiments, an alert could be triggered when an EDA measurement rises between 10-90% compared with an expected EDA measurement. In some embodiments, an alert could be triggered when an EDA measurement rises between 10-80% compared with an expected EDA measurement. In some embodiments, an alert could be triggered when an EDA measurement rises between 10-70% compared with an expected EDA measurement. In some embodiments, an alert could be triggered when an EDA measurement rises between 10-60% compared with an expected EDA measurement. In some embodiments, an alert could be triggered when an EDA measurement rises between 10-50% compared with an expected EDA measurement. In some embodiments, an alert could be triggered when an EDA measurement rises between 10-40% compared with an expected EDA measurement. In some embodiments, an alert could be triggered when an EDA measurement rises between 10-30% compared with an expected EDA measurement. In some embodiments, an alert could be triggered when an EDA measurement rises between 10-20% compared with an expected EDA measurement. In some embodiments, an alert could be triggered when an EDA measurement rises between 20-90% compared with an expected EDA measurement. In some embodiments, an alert could be triggered when an EDA measurement rises between 30-80% compared with an expected EDA measurement. In some embodiments, an alert could be triggered when an EDA measurement rises between 40-70% compared with an expected EDA measurement. In some embodiments, an alert could be triggered when an EDA measurement rises between 50-60% compared with an expected EDA measurement.

In some embodiments, the system of the present invention is configured to use, e.g., but not limited to, real time HRV obtained from data captured from a wristband as at least one signal, and generates an alert for a predicted epileptic seizure.

In some embodiments, the system can include parameters such as, but not limited to, the disease background of the patient when calculating the expected values of the HRV throughout the night. In some embodiments, a correlation exists between suffering from epilepsy and reduced HRV; specifically, an overall decline in HRV in both epileptic and non-epileptic populations can occur, with a greater decrease in participants with epilepsy.

Epilepsies

Epilepsies are a spectrum of brain disorders ranging from severe, life-threatening and disabling, to benign disorders. In epilepsy, the normal pattern of neuronal activity becomes disturbed, causing strange sensations, emotions, and behavior. This disturbed neuronal activity sometimes causes convulsions, muscle spasms, and loss of consciousness. The epilepsies have many possible causes and there are several types of seizures. Seizures can be caused by any disruption to the normal pattern of neuron activity. Examples of neuronal activity disruption are: illness, brain damage, and abnormal brain development. Epilepsy can also develop due to an abnormality in brain wiring, an imbalance of nerve signaling chemicals (neurotransmitters), changes in brain cell channels, or some combination of these and other factors. Having a single seizure as the result of a high fever (called febrile seizure) or head injury does not necessarily mean that a person has epilepsy. For about 70 percent of those diagnosed with epilepsy, seizures can be controlled with modern medicines and surgical techniques.

In some embodiments, the present invention is focused on 30% of a patient population diagnosed with epilepsy which suffers from seizures that are not able to be controlled with modern medicines and surgical techniques. In some embodiments, the present invention is focused on those suffering from night seizures. In some embodiments of the present invention, a population of patients diagnosed with epilepsy is at risk for abnormally prolonged seizures or sudden unexplained death. In some embodiments, the present invention is a system that can predict an upcoming or ongoing seizure and provide an alert of an ongoing seizure. In some embodiments of the present invention, the seizure is a nocturnal (night) seizure. In some embodiments of the present invention, the occurrence of a night seizure can pose a risk on the life of the patient. In some embodiments, the present invention identifies abnormalities and changes in the heartbeat, heartbeat variability and other changes in the period before and during epileptic seizures.

In some embodiments of the present invention, in addition to HRV and rapid, sudden hand or other body part movement, additional parameters can be used for the prediction of an epileptic seizure or at least create an alert once the epilepsy seizure occurs.

In some embodiments of the present invention, HRV is used to detect autonomic dysfunction. In some embodiments of the present invention, a dysfunction of autonomic nervous system is associated with increased mortality after myocardial infarction in the general population and also in patients with epileptic seizures. In some embodiments of the present invention, HRV is categorized into high frequency power (e.g., HF; 0.15-0.40 Hz) and low frequency power (e.g. LF;

0.04-0.15 Hz), and both categorizations depend on oscillatory frequency and development mechanism. In some embodiments of the present invention, the LF component is influenced by both parasympathetic and sympathetic regulation. In some embodiments of the present invention, the HF component and LF/(HF+LF) ratio in normalized units (LF %) reflect the extent of vagal (parasympathetic) and sympathetic regulation of the heart, respectively.

An embodiment of the present invention is an alert system, which incorporates at least one of the following: 1) heart rate, 2) HRV, 3) stress level and daily stressful and other activities/events the user experienced, 4) food intake and medication of the user and 5) the heart rate and HRV parameters of the user. In an embodiment of the present invention, for each point in time and in particular the night, the system calculates an expected hand and body movement, expected heart rate and HRV, and for extreme deviations from these values, the system creates an epilepsy alert. In an embodiment of the present invention, a system does not require a camera to view the movement of the body of the user. In another embodiment of the present invention, a digital camera (with or without infrared to assist in night viewing) connected to a computer is added to the system, to detect movement. In some embodiments of the present invention, sudden movement (that is calculably more extreme than expected movements of the user during the day or night) is used as an additional measurement to detect seizures.

An embodiment of the present invention is shown in FIG. 3. In the embodiment, a combination of a wristband (or armband, or other wearable sensor) 710 worn by a user 720, which can communicate by a communication standard such as Bluetooth 730 with a mobile device such as an iPhone 740. In an embodiment of the present invention, an application resides on the mobile device 740 and captures the biosignal of the heart rate and HRV from the wristband 710. In another embodiment, additional biosignals captured from the body of the user from the sensors on the wristband including, but not limited to, tremor, blood oxygen, galvanic response, and skin temperature.

An embodiment of the present invention is also shown in FIG. 4. In an embodiment, HRV is configured to be calculated at the mobile device if the frequency of the beat to beat heart sampling is sufficiently high, for example at 108 hz. In another embodiment, information from an application can be sent to a Data Center 750 where Big Data analysis is configured to be managed. In an embodiment, data is managed by comparison to other user data, benchmarking to historical data, back-testing, storage, routing of data to medical personnel is conducted.

In an embodiment of the present invention, a sudden change in HRV or at one of its components (e.g., the LH or HF components) is an indication of a forthcoming epileptic seizure. In an embodiment of the present invention, an alert is configured to trigger an alarm on the mobile phone. In another embodiment, the present invention alerts the user to wake-up. In another embodiment, the present invention sends at least one alert to a medical team or a family member of the user.

An embodiment of the present invention is shown in FIG. 5. In an embodiment, an initial setting up phase 9.1, where the user configures his preference set, containing his medications, including dosing, morning medication. In another embodiment, at step 9.2. the user enters his last food intake before going to sleep, as well as the information related to current stress level (if, for example, the wrist band was not worn during the day and the information was not captured during the day by the system already), and events that may have been contributing to stress level throughout the day (such events may also have been documented by the user on the system during the day. In another embodiment, at stage 9.3, information from the wristband is continuously analyzed. In another embodiment, such information includes multi-parameters from at least one of the following measurements: beat to beat heart rate, HRV and its components, oxygen level, skin temperature, hand and body movement (as captured by the accelerometer), galvanic skin response. In another embodiment, such data is analyzed for changes versus what would have been expected for the same time during the night sleep for the same user when compared to the benchmark on the data base located at the mobile device 740 and/or the data center 750 and/or the cpu level located on the wrist band 710. In another embodiment, a comparison of the calculated expected values versus the actual values is accounted. In another embodiment, the prior information known about the user, such as the food eaten in the meal prior to going to sleep as tested prior to going to sleep and in the tests measured on the day preceding to it are accounted.

In another embodiment, when according to the comparison system 9.5 there is a significant change from what would have been expected, an alert system would be triggered, to wake up the person 9.6.1, to alert the family, 9.6.2 and/or the medical team 9.6.3.

In another embodiment of the present invention, the triggers for an alarm are configured to be adjusted based on the lifestyle and habits of the user. In an embodiment, the user could enter the food the user eats before going to sleep, medications and other personal settings that could affect the likelihood and timing of an epileptic attack.

In an embodiment of the present invention, the amount and type of food and medications prior to going to sleep will have an impact on the probability of epilepsy and the time during sleep, if at all, of an epilepsy event to occur. In an embodiment, additional events on the day prior to the night sleep influence the likelihood of epilepsy to occur. In an embodiment, levels of stress are measured by the wristband using HRV previously measured (during the preceding day(s)), as captured by the application. In an embodiment, the higher the level of stress, the higher the likelihood for occurrence of an event of epilepsy.

Illustrative Operating Environments

FIG. 1 illustrates one embodiment of an environment in which the system of the present invention may operate. However, not all of these components may be required to practice the invention, and variations in the arrangement and type of the components may be made without departing from the spirit or scope of the present invention. In some embodiments, the system and method may include a large number of members and/or concurrent transactions. In other embodiments, the system and method are based on a scalable computer and network architecture that incorporates varies strategies for assessing the data, caching, searching, and database connection pooling. An example of the scalable architecture is an architecture that is capable of operating multiple servers.

In embodiments, members of the computer system 102-104 include virtually any computing device capable of receiving and sending a message over a network, such as network 105, to and from another computing device, such as servers 106 and 107, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices 102-104 are any device that is capable of connecting using a wired or wireless communication medium such as a PDA, POCKET PC, wearable computer, and any other device that is equipped to communicate over a wired and/or wireless communication medium.

In embodiments, each member device within member devices 102-104 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, programming may include either Java, .Net, QT, C, C++ or other suitable programming language.

In embodiments, member devices 102-104 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a Proprietary protocol.

In embodiments, network 105 may be configured to couple one computing device to another computing device to enable them to communicate. In some embodiments, network 105 may be enabled to employ any form of computer readable media for communicating information from one electronic device to another. Also, in embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

FIG. 2 shows another exemplary embodiment of the computer and network architecture that supports the method and system. The member devices 202a, 202b thru 202n shown each at least includes a computer-readable medium, such as a random access memory (RAM) 208 coupled to a processor 210 or FLASH memory. The processor 210 may execute computer-executable program instructions stored in memory 208. Such processors comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 210 of client 202a, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Member devices 202a-n may also comprise a number of external or internal devices such as a mouse, a CD-ROM, DVD, a keyboard, a display, or other input or output devices. Examples of client devices 202a-n may be personal computers, digital assistants, personal digital assistants, cellular phones, mobile phones, smart phones, pagers, digital tablets, laptop computers, Internet appliances, and other processor-based devices. In general, a client device 202a may be any type of processor-based platform that is connected to a network 206 and that interacts with one or more application programs. Client devices 202a-n may operate on any operating system capable of supporting a browser or browser-enabled application, such as Microsoft™, Windows™, or Linux. The client devices 202a-n shown may include, for example, personal computers executing a browser application program such as Microsoft Corporation's Internet Explorer™, Apple Computer, Inc.'s Safari™, Mozilla Firefox, and Opera. Through the client devices 202a-n, users, 212a-n communicate over the network 206 with each other and with other systems and devices coupled to the network 206. As shown in FIG. 1B, server devices 204 and 213 may be also coupled to the network 206.

In some embodiments, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

For purposes of the instant description, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the instant invention offers/manages the cloud computing/architecture as, but not limiting to: infrastructure a service (IaaS), platform as a service (PaaS), and software as a service (SaaS). FIGS. 8 and 9 illustrate schematics of exemplary implementations of the cloud computing/architecture.

Of note, the embodiments described herein may, of course, be implemented using any appropriate computer system hardware and/or computer system software. In this regard, those of ordinary skill in the art are well versed in the type of computer hardware that may be used (e.g., a mainframe, a mini-computer, a personal computer ("PC"), a network (e.g., an intranet and/or the internet)), the type of computer programming techniques that may be used (e.g., object oriented programming), and the type of computer programming languages that may be used (e.g., C++, Basic, AJAX, Javascript). The aforementioned examples are, of course, illustrative and not restrictive.

In some embodiments, the present invention provides a method of epileptic-directed treatment for an epileptic seizure, including delivering an alert to a user and/or a third party (e.g., but not limited to, a medical professional, a family member, etc.) of an imminent epileptic seizure so as to allow the user and/or third party to administer a medication to treat the user to reduce the occurrence and/or severity of the epileptic seizure by between 10-99% (e.g., but not limited to, 10%, 20%, 30%, 40%, 50%, 60%, 70%, 80%, 90%, 95%, etc.) In some embodiments, epileptic-directed medications such as, but not limited to, Dilantin/phenytek, phenobarbital, tegretol, mysoline, zarontin, depakene, Depakote, valium, tranzene, klonopin, felbatol, gabitril, keppra, lamictal, lyrica, Neurontin, Topamax, trileptal, zonegran, or any combination thereof, are administered to a user (after the alert is delivered to the user) so as to treat the imminent epileptic attack. In some embodiments, Dilantin is administered to a user orally at between 100 mg-400 mg a dose. In some embodiments, phenobarbital is administered to a user orally, intramuscularly (IM), or intravenous (IV) at between 30 to 120 mg/day. In some embodiments, tegretol is administered to a user orally at between 100-200 b.i.d. (two times a day) or 0.5-1 teaspoon q.i.d. (single dose) for suspension (200-400 mg/day). In some embodiments, mysoline is administered to a user orally at between 50 to 250 mg t.i.d. In some embodiments, zarontin is administered to a user orally at between 250 mg to 500 mg a day. In some embodiments, depakene/valproic acid is administered to a user orally at between 250 mg-1.25 mg a day. In some embodiments, depakote is administered to a user orally at between 10-60 mg/kg/day. In some embodiments, valium is administered to a user orally at between 2 mg-10 mg, 3 or 4 times daily. In some embodiments, tranzene is administered to a user orally at between 15 to 90 mg in divided doses. In some embodiments, klonopin is administered to a user orally at between 0.5 mg to 1.5 mg/day. In some embodiments, felbatol is administered to a user orally at between 1200-3600 mg/day. In some embodiments, gabitril is administered to a user orally at between 2-16 mg daily. In some embodiments, keppra is administered to a user orally at between 35-3000 mg daily. In some embodiments, lamictal is administered to a user orally at between 25 mg/day-500 mg/day. In some embodiments, lyrica is administered to a user orally at between 150-600 mg/day. In some embodiments, Neurontin is administered to a user orally at between 100-3600 mg/day. In some embodiments, Topamax is administered to a user orally at between 50-400 mg/day (administered in two doses). In some embodiments, trileptal is administered to a user orally at between 600 mg/day-1200 mg/day. In some embodiments, zonegran is administered to a user orally at between 100-600 mg/day.

In some embodiments, the present invention provides a method of epileptic-directed treatment for an epileptic seizure, including delivering an alert to a user and/or a third party (e.g., but not limited to, a medical professional, a family member, etc.) of an imminent epileptic seizure so as to allow the user and/or third party to administer a breathing/relaxation exercise, e.g., breathing normalization and/or progressive relaxation to reduce the occurrence or severity of the imminent epileptic seizure. In some embodiments, electrotherapy can be administered to a user to treat an imminent epileptic attack.

In some embodiments, the instant invention provides for a computer system, including: a) at least one server having software stored on a non-transient computer readable medium; where, upon execution of the software, the at least one server is at least configured to: i) receiving, an input from a user, where the input includes user data consisting of: food intake of the user, medication intake by the user, stress related events in the preceding day, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, an input from a user or from his medical record, where the input comprises user data consisting of: food intake of the user, stress related events in the preceding day, medication intake by the user (including, for example, but not limited to, insulin), medical measurements (including glucose reading), or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer system, including: a) at least one server having software stored on a non-transient computer readable medium; where, upon execution of the software, the at least one server is at least configured to: i) receiving, in real-time, an input from a user, where the input includes user data consisting of: food intake of the user, medical measurements by the user (such as, but not limited to, blood pressure reading and/or glucose reading), medication intake by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, in real-time, an input from a user, where the input comprises user data consisting of: food intake of the user, medication intake by the user, recent medical readings (such as, but not limited to, glucose reading or blood pressure and the readings taken within, e.g., but not limited to, between 1 second and 1 hour (e.g., 1 second, 1 minute, 5 minutes, 10 minutes, 15 minutes, etc.)) or any combination thereof; ii) receiving, in real-time, physiological data representative of at least one physiological measurement of at least one physiological characteristic of the user, where the at least one physiological characteristic is selected from the group consisting of: heart rate, low frequency heart rate variability, high frequency heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

An embodiment of the present invention is a computer-implemented method, comprising: receiving, by a specifically programed processing computer system, from an electronic monitoring system, at least two of the following: i) a first data from the electronic monitoring system, wherein the first data from the electronic monitoring system is selected from the group consisting of: a first heart beat, a first heart beat variability, a first low frequency heart beat variability, a first high frequency heart beat variability, a first level of movement, and a first blood saturation level, and ii) a second data from the electronic monitoring system, wherein the second data from the electronic monitoring system is selected from the group consisting of: a second heart beat, a second heart beat variability, a second low frequency heart beat variability, a second high frequency heart beat variability, a second level of movement, and second blood saturation level; comparing the first data from the electronic monitoring system to the second data from the electronic monitoring system, wherein the electronic monitoring system identifies at least one deviation of a user, wherein the user is patient diagnosed with epilepsy; sending, by the specifically programed processing computer system, at least one alert to at least one designated responder, wherein the at least one designated responder is selected from the group consisting of: a member of a medical team and a member of the family; generating, in response to the receiving the alert by the specifically programed processing computer system, a notification to the at least one designated responder; sending, by the specifically programed processing computer system, the notification to the at least one designated responder; receiving, by the at least one designated responder, the notification; wherein the at least one designated responder receives the notification by the specifically programed processing computer system.

In some embodiments, the instant invention provides for a computer system, including: a) at least one server having software stored on a non-transient computer readable medium; where, upon execution of the software, the at least one server is at least configured to: i) receiving, in real-time, physiological data representative of a first physiological measurement of at least one physiological characteristic of the user, wherein the at least one physiological characteristic is selected from the group consisting of: heart rate, heart rate variability, oxygen saturation, temperature, hand movement, galvanic skin response, or any combination thereof; ii) receiving, in real-time, physiological data representative of a second physiological measurement of at least one physiological characteristic of the user, wherein the at least one physiological characteristic is selected from the group consisting of: heart rate, heart rate variability, oxygen saturation, temperature, hand movement, galvanic skin response, or any combination thereof; iii) comparing, in real-time, the first physiological measurement of the user to the second physiological measurement of the user; iv) based on the comparing, determining, in real-time, that a difference between the first physiological measurement of the user and the second physiological measurement is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, in real-time, physiological data representative of a first physiological measurement of at least one physiological characteristic of the user, wherein the at least one physiological characteristic is selected from the group consisting of: heart rate, heart rate variability, oxygen saturation, temperature, hand movement, galvanic skin response, or any combination thereof; ii) receiving, in real-time, physiological data representative of a second physiological measurement of at least one physiological characteristic of the user, wherein the at least one physiological characteristic is selected from the group consisting of: heart rate, heart rate variability, oxygen saturation, temperature, hand movement, galvanic skin response, or any combination thereof; iii) comparing, in real-time, the first physiological measurement of the user to the second physiological measurement of the user; iv) based on the comparing, determining, in real-time, that a difference between the first physiological measurement of the user and the second physiological measurement is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a method of treatment, including: when at least one alert generated by at least one wearable computing device is received by a user, administering an effective amount of an epileptic-directed treatment to the user so as to reduce a severity or occurrence of an imminent epileptic seizure, where the epileptic-directed treatment is selected from the group consisting of an epileptic-directed medication, electrotherapy, relaxation therapy, and breathing therapy, where the at least one alert is generated regarding at least one physiological condition; where the at least one alert is generated when a measurement of the at least one physiological condition is higher than at least one predetermined threshold measurement, where the at least one physiological condition of the user is selected from the group consisting of: heart rate, heart rate variability, oxygen saturation, PPG signal, temperature, hand movement, galvanic skin response, or any combination thereof, where at least one alert is transmitted to at least one of: the user, at least one family member, at least one medical practitioner, or any combination thereof, and where, when the measurement of the at least one physiological condition is smaller than the predetermined threshold measurement, continuing to measure the at least one physiological condition of the user. In some embodiments, the at least one alert is further generated when a first physiological measurement is compared to a second physiological measurement, the second physiological measurement is selected from the group consisting of: heart rate, heart rate variability, oxygen saturation, temperature, hand movement, galvanic skin response, PPG signal, or any combination thereof, the at least one alert is generated when a difference between the first physiological measurement of the user and the second physiological measurement is higher than a predetermined threshold value.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A computer system, comprising:
   a) at least one wearable garment, comprising a plurality of non-invasive sensors;
      i) wherein the plurality of non-invasive sensors are configured to continuously acquire, in real-time, a plurality of biosignals from a person wearing the at least one wearable garment;
      ii) wherein the plurality of biosignals are representative of heart rate variability (HRV), electrodermal activity (EDA), and motor movement;
      iii) wherein the at least one wearable garment is configured to wirelessly transmit the plurality of biosignals to at least one portable computing device associated with the person wearing the at least one wearable garment;
   b) the at least one portable computing device having software stored on a non-transient computer readable medium;
   wherein, upon execution of the software, the at least one portable computing device is at least configured to:
      i) receiving, in real-time, a current set of the plurality of biosignals which are representative of a current value of at least one power spectral component of the heart rate variability (current HRV value), a current value of the electrodermal activity (current EDA value), and current motor movement of the person;
      ii) dynamically calculating, in real-time, based on the current set of the plurality of biosignals, the current HRV value and the current EDA value;
      iii) dynamically determining, in real-time, based on the current set of the plurality of biosignals, the current motor movement of the person;
      iv) dynamically comparing, in real-time,
         1) the current HRV value to at least-a population historical HRV value of a population of people, wherein each person of the population of people has at least one characteristic associated with at least one of a current psychological condition of the person and a current physiological condition of the person and wherein the at least one characteristic of the current physiological condition of the person is dependent on a food intake of the person;
         2) the current EDA value to at least a population historical EDA value of the population of people; and
         3) the current motor movement of the person to a historical motor movement of the person at the particular time period;
      v) based on the comparing, dynamically determining, in real-time, a presence of at least one health-related condition;
      vi) dynamically generating, in real-time, at least one alert when the presence of the at least one health-related condition has been determined; and
      vii) at least one of:
         1) dynamically appraising, via the at least one portable computing device, the person about the at least one alert, and
         2) dynamically and wirelessly transmitting, in real-time, the at least one alert to at least one of: a first electronic device associated with the at least one family member, a second electronic device associated with at least one medical practitioner, or any combination thereof.

2. The computer system of claim 1, wherein the at least one portable computing device is further configured to dynamically transmitting, in real-time, the at least one alert to a third electronic device; and therein the third electronic device is configured to reside in the at least one wearable garment.

3. The computer system of claim 1, wherein the first electronic device and the second electronic device are portable electronic devices.

4. The computer system of claim 1, wherein the dynamically appraising, via the at least one portable computing device, the person about the at least one alert comprises dynamically outputting at least one of at least one visual alert and at least one audio alert.

5. The computer system of claim 1, wherein the at least one characteristic of the current psychological condition of the person is a stress level.

6. The computer system of claim 1, wherein the at least one characteristic of the current physiological condition of the person is a heart rate.

7. A computer-implemented method, comprising:
   providing at least one wearable garment, comprising a plurality of non-invasive sensors;
      i) wherein the plurality of non-invasive sensors are configured to continuously acquire, in real-time, a plurality of biosignals from a person wearing the at least one wearable garment;
      ii) wherein the plurality of biosignals are representative of heart rate variability (HRV), electrodermal activity (EDA), and motor movement;
      iii) wherein the at least one wearable garment is configured to wirelessly transmit the plurality of biosignals to at least one portable computing device associated with the person wearing the at least one wearable garment;
   programming the at least one portable computing device with a software to be stored on a non-transient computer readable medium;
   wherein, upon execution of the software, the at least one portable computing device is at least configured to:
      i) receiving, in real-time, a current set of the plurality of biosignals which are representative of a current value of at least one power spectral component of the heart rate variability (current HRV value), a current value of the electrodermal activity (current EDA value), and current motor movement of the person;
      ii) dynamically calculating, in real-time, based on the current set of the plurality of biosignals, the current HRV value and the current EDA value;
      iii) dynamically determining, in real-time, based on the current set of the plurality of biosignals, the current motor movement of the person;
      iv) dynamically comparing, in real-time,
         1) the current HRV value to at least a population historical HRV value of a population of people, wherein each person of the population of people has at least one characteristic associated with at least one of a current psychological condition of the person and a current physiological condition of the person and wherein the at least one characteristic of the current physiological condition of the person is dependent on a food intake of the person;

2) the current EDA value to at least a population historical EDA value of the population of people; and
3) the current motor movement of the person to a historical motor movement of the person at the particular time period;

v) based on the comparing, dynamically determining, in real-time, a presence of at least one health-related condition;

vi) dynamically generating, in real-time, at least one alert when the presence of the at least one health-related condition has been determined; and vii) at least one of:
1) dynamically appraising, via the at least one portable computing device, the person about the at least one alert, and
2) dynamically and wirelessly transmitting, in real-time, the at least one alert to at least one of: a first electronic device associated with the at least one family member, a second electronic device associated with at least one medical practitioner, or any combination thereof.

8. The method of claim 7, wherein the at least one portable computing device is further configured to dynamically transmitting, in real-time, the at least one alert to a third electronic device; and therein the third electronic device is configured to reside in the at least one wearable garment.

9. The method of claim 7, wherein the first electronic device and the second electronic device are portable electronic devices.

10. The method of claim 7, wherein the dynamically appraising, via the at least one portable computing device, the person about the at least one alert comprises dynamically outputting at least one of at least one visual alert and at least one audio alert.

11. The method of claim 7, wherein the at least one characteristic of the current psychological condition of the person is a stress level.

12. The method of claim 7, wherein the at least one characteristic of the current physiological condition of the person is a heart rate.

* * * * *